Figure 1:
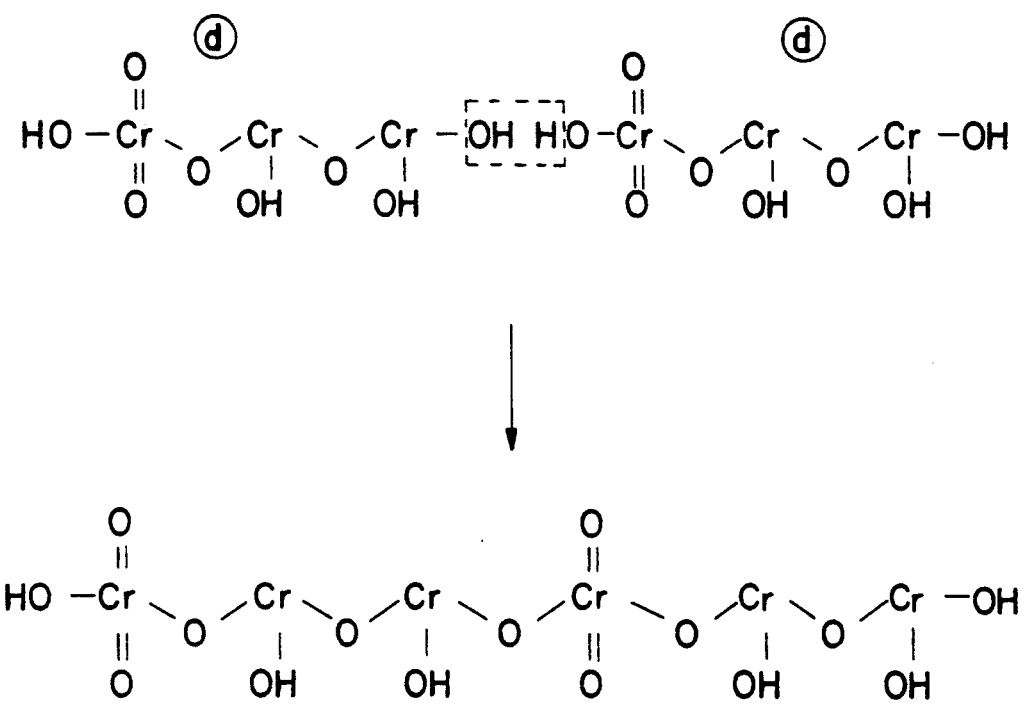

United States Patent [19]

Yoshitake et al.

[11] Patent Number: 5,141,575
[45] Date of Patent: Aug. 25, 1992

[54] SURFACE TREATMENT FOR ZINCIFEROUS SURFACES

[75] Inventors: Noriaki Yoshitake; Kenshi Saeki; Takumi Honda; Takao Ogino, all of Kanagawa, Japan

[73] Assignee: Henkel Corporation, Ambler, Pa.

[21] Appl. No.: 505,337

[22] Filed: Apr. 5, 1990

[30] Foreign Application Priority Data

Apr. 7, 1989 [JP] Japan .................... 1-89416

[51] Int. Cl.$^5$ ............................. C23C 22/53
[52] U.S. Cl. .................... 148/247; 148/248; 148/258
[58] Field of Search .......... 148/258, 247, 248

[56] References Cited

U.S. PATENT DOCUMENTS 4,971,636  11/1990  Watanabe ............... 148/258
5,039,360  8/1991   Buegarolas ............. 148/258

FOREIGN PATENT DOCUMENTS 2180263  9/1986  United Kingdom .

*Primary Examiner*—Sam Silverberg
*Attorney, Agent, or Firm*—Ernest G. Szoke; Wayne C. Jaeschke; Norvell E. Wisdom, Jr.

[57] ABSTRACT

Zinciferous surfaces, particularly those of galvanized steel, may be effectively protected against corrosion, either as treated or after painting, while remaining easy to weld, by contact with an aqueous solution containing chromium in both +6 and +3 valence states, phosphate, a tertiary alcohol or similar oxidation stable, water soluble organic compound as a wetting agent, and a silane coupling agent, followed by drying with a film from the solution still in place on the surface. A thin coating containing 10–200 mg/m$^2$ of chromium is formed on the surface to provide a protective layer that is also an excellent base for paint.

20 Claims, 2 Drawing Sheets

* = REDUCTION BY METHANOL AND SOLVENT

SURFACE TREATMENT FOR ZINCIFEROUS SURFACES

FIELD OF THE INVENTION

This invention relates to a treatment method which is capable of developing a chromium containing film that provides an excellent base for paint, by having both good paint adherence and good corrosion resistance after painting, as well as excellent corrosion resistance, alkali resistance, and ease of welding, because of relatively low electrical resistance, when left unpainted. Treatment according to the invention is applied to surfaces containing zinc as a predominant constituent, particularly to surfaces of electrogalvanized steel sheet, zinc-alloy electroplated steel sheet, and galvannealed steel sheet (collectively denoted as "zinc-plated steel sheet" below).

STATEMENT OF RELATED ART

While chromate treatment solutions originally consisted essentially of aqueous solutions of chromic acid or dichromic acid, a number of methods have been proposed for the formation of films that are more resistant to the acid and alkali treatments which may be conducted after chromate film formation. This art is discussed below.

The invention of Japanese Patent Application Laid Open [Kokai] Number 50-158535[158,535/75] concerns a method for the formation of solution resistant chromate films on the surface of zinc-plated steel sheet. In this reference, the chromate solution contains chromic anhydride, phosphoric acid, and water-soluble or water-dispersible polymer, and the $Cr^{6+}$ in this treatment bath is at least 70 % reduced to $Cr^{3+}$ by a reductant such as ethylene glycol. However, although the film formed by the implementation of this invention is excellent in terms of low solubility, corrosion resistance, and suitability as a base for paint, it nevertheless suffers from the problem of poor weldability because it contains polymer.

The chromate bath taught in Japanese Patent Publication Number 61-58522[58,522/86] contains specified amounts of chromic acid, reduced chromic acid, and silica sol components. However, when a surface-treated steel sheet carrying the chromate film formed by the method of this invention is processed for painting, most of the hexavalent chromium in the chromate film is easily eluted by the alkali rinse prior to painting. Thus, the corrosion resistance of the film is then lowered due to its poor alkali resistance. Also, because the film contains silica, its weldability, for example, its spot weldability, is poor.

Japanese Patent Application Laid Open Numbers 58-22383[22,383/83] and 62-83478[83,478/87] are examples of the disclosure of the use of silane coupling agents as reductants for the hexavalent chromium in chromate treatment solutions. While the films formed by the methods of these references provide excellent paint bondability, the chromate film formed by the method of the former reference has a poor alkali resistance because it does not contain silica or organic polymer. In the latter reference, the spot weldability is unsatisfactory because colloidal silica is present. When the properties of the individual components in these prior chromate treatment methods are examined, one finds that organic polymer and silica sol, while increasing the corrosion resistance, also tend to degrade the weldability. Silane coupling agents tend to make the chromate film's corrosion resistance unstable because they tend to reduce the $Cr^{6+}$.

DESCRIPTION OF THE INVENTION AND DRAWINGS

It is an object of the present invention to solve the problems manifested by the prior art of chromate treatment methods for zinc-plated steel sheet, while retaining most or all of the benefits of these prior art methods, by a method for the formation of a chromium containing film which has an excellent corrosion resistance, alkali resistance, processability, and uniformity of application and produces a surface that is readily welded and serves as an excellent base for paint.

In this description, except in the working examples and where otherwise expressly noted, all numbers describing amounts of materials use or conditions of reaction or use are to be understood as modified by the term "about".

One embodiment of the present invention is a process for treating objects with a zinciferous surface, preferably sheets of zinc-plated steel, by contact between the surface of the treated object and a liquid solution composition that comprises, or preferably consists essentially of, water and the following components:

(A) from 3.0 to 50 grams per liter ("g/L") of the composition of hexavalent chromium;

(B) from 2.0 to 40 g/L of trivalent chromium;

(C) from 1.0 to 100 g/L of phosphate ion ($PO_4^{3-}$);

(D) from 3 to 50 g/L of at least one type of organic material selected from tertiary alcohols with 4–8 carbon atoms per molecule and acetonitrile; and (E) an amount of silane coupling agent such as to yield a molar ratio of 0.05 to 0.30 between the total of silane coupling agent and the hexavalent chromium concentration in the composition; and, optionally, (F) from 0.2 to 10 g/L of $Zn^{+2}$ ions; and (G) a component of simple and/or complex fluoride ions in an amount to give from 0.2 to 8 g/L stoichiometric equivalent of fluoride, the $Cr^{3+}$weight ratio in the solution being 0.25 to 1.5 and the weight; $CR^{6+}$ ratio between phosphate ion and total chromium $\{PO_4^{3-}/(Cr^{6+}+Cr^{3+})\}$ in the solution being 0.1 to 1.2. After this, the treated surface is dried while some of the non-volatile constituents of the liquid composition noted above remain on the surface, to form on the surface a chromium containing film with a chromium content of 10 to 200 milligrams per square meter ("mg/m$^2$") of surface. It is to be understood that necessary counter-ions to the constituents specified above in ionic form are also present in the solution composition used according to this invention.

The composition of the aqueous solution used by the method of the present invention is discussed in more detail below.

This solution uses water as its solvent, and it contains 3.0 to 50 g/L of $Cr^{6+}$ and 2 0 to 40 g/L of $Cr^{3+}$ as essential components. The formation of a satisfactorily corrosion-resistant chromium containing film becomes problematic when the $Cr^{6+}$ falls below 3.0 g/L or the $Cr^{3+}$ falls below 2.0 g/L. Conversely, when the $Cr^{6+}$ exceeds 50 g/L or the $Cr^{3+}$ exceeds 40 g/L, the chromate bath will have a high viscosity and a poor stability, and it becomes difficult to control the quantity of chromium deposited in the surface coating formed.

Furthermore, a crucial element of the composition is the ratio between $Cr^{6+}$ and $Cr^{3+}$. It is essential that the chromium ratio ($Cr^{3+}/Cr^{6+}$) fall within the range of 0.25 to 1.5. When the chromium ratio falls below 0.25, the oxidizing tendency of the $Cr^{6+}$ content in the chromate bath is increased. As a result, when the silane coupling agent is added to such a bath, reduction of the $Cr^{6+}$ in the chromate bath by the silane coupling agent tends to develop rather readily, and the chromate bath is heated by this. As a consequence, the rate of the $Cr^{6+}$ reduction reaction by the solvent in the chromate bath and solvent volatilization are both increased, causing a decline in the quality of the chromate bath. When the chromium ratio exceeds 1.5, the chromate bath evidences a tendency to gel, and the corrosion resistance of the chromium containing surface film is also reduced. The chromium ratio can be controlled by the addition as necessary of a reductant such as ethanol, methanol, oxalic acid, starch, sucrose, and the like.

Another component in the solution composition of the present invention is $PO_4^{3-}$ at 1.0 to 100 g/L. This $PO_4^{3-}$ is preferably added as orthophosphoric acid ($H_3PO_4$). When the $PO_4^{3-}$ content falls below 1.0 g/L, the corrosion resistance and alkali resistance of the surface coating formed on the zinciferous surfaces treated are reduced. Conversely, exceeding 100 g/L promotes the rapid reduction of the $Cr^{6+}$ in the solution by the silane coupling agent, and the quality of the solution is degraded as a result.

A particularly important aspect of the $POhd 4^{3-}$ content is its ratio relative to the quantity of total chromium ($Cr^{6+} + Cr^{3+}$) in the solution, and a $PO_4^{3-}/\text{total Cr}$ ratio within the range of 0.1 to 1.2 is preferred. When this ratio falls below 0.1, the alkali resistance and corrosion resistance of the surface film formed during a process according to the invention tend to decline. Conversely, at values exceeding 1.2, reduction of the $Cr^{6+}$ in the chromate bath by the silane coupling agent proceeds very easily, with the result that the $Cr^{6+}$ in the chromate bath is substantially or almost completely reduced to $Cr^{3+}$ prior to application. As a consequence, the quality of the chromate bath is reduced, and it becomes difficult to form a coating which satisfies the object of the present invention.

In order to improve the uniformity of coating achieved with the invention, the solution used contains 3 to 50 g/L of another component which functions as a wettability improver: one compound or, if desired, a mixture of compounds selected from $C_4$-$C_8$ tertiary alcohols and acetonitrile. Each of these compounds has a relatively high stability with regard to the $Cr^{+6}$ present in the chromate bath at bath temperatures below approximately 35 degrees Centigrade, while none adversely affects the quality of the treatment film formed to any significant degree. At the same time, each can function to increase the wettability of the chromate bath on the plated surface. Accordingly, each can contribute to increasing the uniformity of chromium coating weight on the treated surface during high-speed operations. The manifestation of such a beneficial effect has not been observed at a concentration below 3 g/L. An increase in effect cannot be expected from further additions in excess of 50 g/L, which are also disadvantageous from the standpoints of economics and the working environment. As a general rule, this organic component is added in greater amounts, the greater the total chromium concentration in the treatment solution, and the greater the application speed. The organic component is preferably selected from tert-butyl alcohol and/or tert-amyl alcohol.

The alkali resistance of the treated surface can be increased by the optional addition of 0.2 to 10 g/L of zinc ions to the aqueous treatment bath. The improvement is vanishingly small at a zinc ion quantity below 0.2 g/L, while exceeding 10 g/L tends to precipitate the $Cr^{3+}$ in the treatment bath. The $Zn^{+2}$ ions are preferably added to the treatment bath in the form of zinc oxide, zinc carbonate, zinc phosphate, or zinc hydroxide.

In addition, complex fluoride may optionally be added to the treatment bath, either by itself or together with zinc. It is preferably added in the range of 0.2 to 8 g/L based on F. Preferred examples of the complex fluoride are fluozirconic acid ($H_2ZrF_6$), fluotitanic acid ($H_2TiF_6$), fluosilicic acid ($H_2SiF_6$), and fluoboric acid ($H_2BF_6$). Their addition in the aforementioned quantity causes the development of etching of the zinc-plated surface by the treatment bath, and the complex fluoride complexes with the eluted metal ion or with this metal ion and any zinc ion added to the bath. This zinc or other metal complex becomes a constituent component of the chromium containing film formed, and contributes to improving the film's uniformity and corrosion resistance. The effects of addition are difficult to note at fluoride quantities below 0.2 g/L, while exceeding 8 g/L lowers the corrosion resistance of the chromium containing film formed.

The aqueous bath as described above should be stored at a temperature of $\leq 35$ degrees Centigrade and preferably at $\leq 25$ degrees Centigrade after addition of the silane coupling agent, and it should be used as soon as possible after formulation. At the point of use, silane coupling agent is preferably first mixed with the chromate bath at a molar ratio referred to the gram-atomic concentration of $Cr^{6+}$ in the chromate bath within the range of 0.05 to 0.30.

While exact composition of the silane coupling agent is not crucial to the invention, silane coupling agents that conform to the following general chemical formula are preferred $Y_yR_rSiX_x$, wherein R represents an alkyl group; X represents a group selected from methoxy and ethoxy groups; Y represents a group selected from a vinyl group, a mercapto group, a glycidoxyalkyl group, or a methacryloxyalkyl group; and each of r, x, and y is an integer independently selectable from 1-3, except that r may also be zero and the sum $r+x+y=4$.

More preferably, the silane coupling agent component is selected from the group consisting of vinyltrimethoxysilane, vinyltriethoxysilane, gamma-mercaptopropyltrimethoxysilane, gamma-glycidoxypropyltrimethoxysilane, gammaglycidoxypropylmethyldimethoxysilane, gamma-methacryloxypropyltrimethcxysilane, gamma-methacryloxypropylmethyldimethoxysilane, and mixtures of any two or more of these.

Silane coupling agents with the above general formula are preferred because they have good solubilities in the aqueous solution used to contact zinc surfaces in a process according to this invention and make a relatively large contribution to improving the corrosion resistance of the protective film formed on the zinc surface.

When the molar ratio of silane coupling agent to $Cr^{+6}$ falls below 0.05, the improvement in the chromium containing film's alkali resistance is negligible. Conversely, when a ratio of 0.3 is exceeded, the chromate bath tends to evidence a gradual decline in stability, i.e., the $Cr^{3+}$ in the chromate bath increases and gelation is facilitated. Use of the silane coupling agent in the molar ratio to $Cr^{+6}$ range of 0.1 to 0.2 is even more preferred.

The treatment bath, mixed with silane coupling agent as explained above, may be coated on the zinc-plated steel sheet or other zinciferous surface by, for example, a roll coater, curtain coater, or any other convenient method that establishes contact between the solution and the surface to be treated and results in a satisfactorily uniform coating of the solution over the surface before drying. While the present invention does not depend critically on the drying conditions, it is preferred that a film with a chromium content of 10 to 200 mg/m² be formed by drying for 5 to 10 seconds at a temperature on the drying surface of 60 to 150 degrees Centigrade. However, the liquid treating solution itself should be maintained at no greater than 35 degrees Centigrade and preferably at no greater than 25 degrees Centigrade after addition of the silane coupling agent to the bath. Treatment solution according to this invention is satisfactorily stable for approximately 1 month at relatively low chromium concentrations, but use within 1 week after the addition of the silane component is strongly preferred for such solutions with high chromium concentrations.

The corrosion resistance of the treated object with a film as formed and the corrosion resistance after painting are both unsatisfactory with less than 10 mg/m² of chromium uptake during a treatment according to this invention. On the other hand, with uptakes exceeding 200 mg/m², it becomes difficult to control the quantity of chromium adherence in the chromate film; the improvement in corrosion resistance reaches an upper limit and further benefits cannot be expected; and paint adherence is reduced because portions of the chromate film are easily removed by external forces when it is so thick.

While the pH of the aqueous chromate bath used in the present invention is not critical, values around 1.0 to 3.0 are preferable.

When the aqueous treating solution is coated on the surface of zinc-plated steel sheet, followed by drying, the $Cr^{6+}$, $Cr^{3+}$, and $PO_4^{3-}$ components in the aqueous chromate bath are believed to react with one another and/or the treated surface, at a rate speeded by the thermal energy supplied by drying. The constituent components of the resulting chromate film are believed to be the colorless materials respectively specified in (a) and (b) below, the green material specified in (c), and the gold colored material specified in (d) and (e).

(a) $Zn(OH)_2$
(b) $Cr(OH)_2$
(c) $CrPO_4 \cdot 4H_2O$
(d) zinc chromate compounds as represented by $ZnO \cdot 3Zn(OH)_2 \cdot CrO_3$; $3Zn(OH)_2 \cdot CrO_3$; $2Zn(OH)_2 \cdot CrO_3$
(e) $Cr(OH)_3 \cdot Cr(OH) \cdot CrO_4$ (chromic chromate)

Taking a trimethoxy group-containing silane coupling agent $YRSi(OCH_3)_3$ as an example, hydrolysis proceeds as in the following chemical equation (1):

$$YRSi(OCH_3)_3 + 3H_2O \rightarrow YRSi(OH)_3\{f\} + 3CH_3OH \qquad (1)$$

Figure 2:
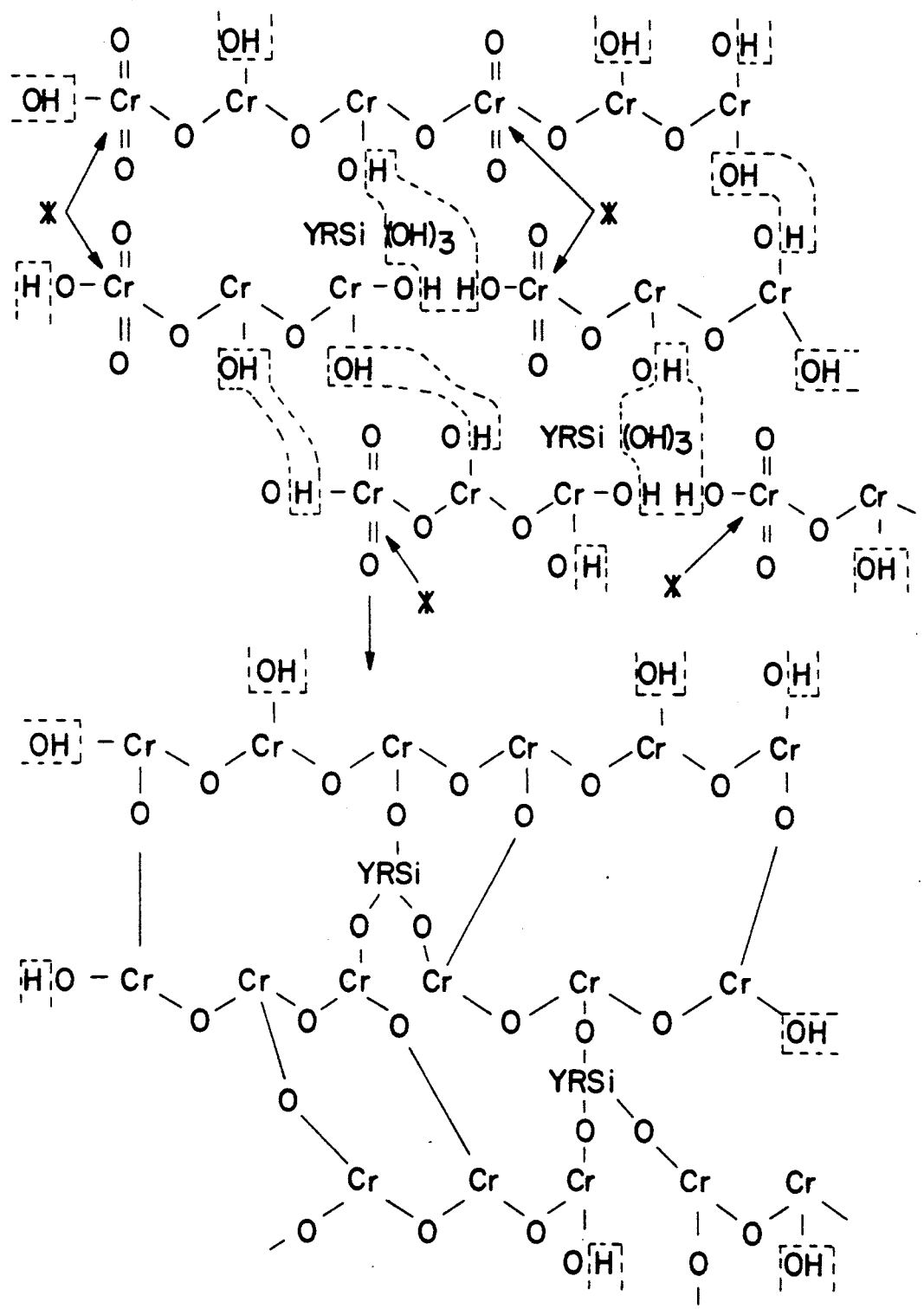

Under the influence of the thermal energy supplied after coating according to this invention, the aforementioned chromic chromate (e), for example, can undergo condensation reactions as depicted by FIG. 1, while at the same time, the chromic chromate is cross linked as depicted in FIG. 2 by the hydrolyzate {f} deriving from the silane coupling agent. Moreover, the hexavalent chromium in the chromic chromate is reduced by the methanol. Therefore, it is thought that a companion macromolecular network structure is formed by the development of complex cross linkages between the chromic chromate and silane coupling agent hydrolyzate. Accordingly, it is thought that each of the aforementioned components (a), (b), (c), and (d) may be present within the structure of the macromolecular, chromium containing coating represented by FIGS. 1 and 2, either in a chain-stopping position or bonded with said macromolecular chromium compound.

With the additional participation of the bonding activity of the silanol group, the chromate film having this network molecular structure exhibits a strong alkali resistance, i.e., the chromium in the film strongly resists elution due to alkali rinsing. Moreover, it is thought that this network molecular structure contributes to increasing both the corrosion resistance and uniformity.

Because this film does not contain silica or an organic macromolecular compound, the electrical resistance of the film is relatively low, so that it is relatively easy to weld surfaces treated according to this invention.

The practice of the present invention may be further understood by consideration of the following non-limiting examples and comparison examples.

EXAMPLES

(1) Preparation of the Treating Bath

Chromate coating bath No. A as reported in Table 1 was prepared as follows: 200 grams ("g") of chromic anhydride ($Cr_2O_6$) was first dissolved in 500 g of water, 86 g of phosphoric acid (75% aqueous solution) and 18 g of methanol were added to the aqueous solution thus obtained, and this was then heated for 1 hour at 80 to 90 degrees Centigrade to cause reduction to a $Cr^{3+}/Cr^{6+}$ weight ratio of 1.0. After cooling, 26 g of tert-butanol and sufficient water to make a total weight of 1 kg were added. This solution is denoted in the following as the aqueous base solution.

The aqueous base solution was then diluted with water to give a total chromium concentration ($Cr^{6+} + Cr^{3+}$) of 40 g/L, along with 10 g/L tert-butanol.

TABLE 1

| | chromate bath (present invention) | | | | | | chromate bath (comparison examples) | | | | |
|---|---|---|---|---|---|---|---|---|---|---|---|
| | No. A | No. B | No. C | No. D | No. E | No. F | No. G | No. H | No. I | No. J | No. K |
| aqueous chromate solution | | | | | | | | | | | |
| $Cr^{6+}$ (g/L) | 20 | 8 | 3 | 30 | 20 | 45 | 20 | 10 | 30 | 20 | 15 |
| $Cr^{3+}$ (g/L) | 20 | 12 | 2 | 15 | 6 | 40 | 15 | 15 | 5 | 20 | 10 |
| $PO_4^{3-}$ (g/L) | 24 | 18 | 1 | 45 | 10 | 90 | — | 20 | 2 | 7 | 10 |
| water-soluble organic solvent (g/L) | t-butanol 10 | t-butanol 5 | t-butanol 3 | t-amyl alcohol 15 | acetonitrile 45 | t-butanol 25 | — | — | t-butanol 10 | — | — |

TABLE 1-continued

|  | chromate bath (present invention) | | | | | | chromate bath (comparison examples) | | | | |
| --- | --- | --- | --- | --- | --- | --- | --- | --- | --- | --- | --- |
|  | No. A | No. B | No. C | No. D | No. E | No. F | No. G | No. H | No. I | No. J | No. K |
| $Cr^{3+}/Cr^{6+}$ | 1.00 | 1.50 | 0.67 | 0.50 | 0.30 | 0.89 | 0.75 | 1.50 | 0.17 | 1.00 | 0.67 |
| $PO_4^{3-}/Cr^{6+} + Cr^{3+}$ | 0.60 | 0.90 | 0.20 | 1.00 | 0.38 | 1.06 | — | 0.80 | 0.06 | 0.18 | 0.40 |
| $Zn^{2+}$ (g/L) (*1) | — | — | — | 3 | — | 7 | — | — | — | — | — |
| fluoride. as $F^-$ (g/L) (*2) | — | — | — | — | 4 | 1 | — | — | — | — | — |
| $SiO_2$ (g/L) (*3) | — | — | — | — | — | — | — | — | — | — | 25 |
| silane coupling agent (g/L) (*4) | (a) 9 | (b) 4 | (c) 0.6 | (a) 18 | (a) 15 | (a) 16 | (a) 9 | — | (a) 4 | — | — |
| silane coupling agent/$Cr^{6+}$ molar ratio | 0.10 | 0.10 | 0.05 | 0.13 | 0.17 | 0.08 | 0.10 |  | 0.03 |  |  |

Notes:
*1 ZnO was used for $Zn^{2+}$.
*2 $H_2ZrF_6$ was used for the fluoride.
*3 The $SiO_2$ was Snowtex O from Nissan Chemical Industries. Ltd.
*4 The silane coupling agents (a)–(c) are defined below. These were added to the aqueous chromate solution with stirring. and this was then applied to the steel sheet to be treated.
(a): gamma-glycidoxypropyltrimethoxysilane
(b): gamma-methacryloxypropyltrimethoxysilane
(c): vinyltriethoxysilane Silane coupling agent (gamma-glycidoxypropyltrimethoxysilane from Toshiba Silicone Company, Limited) was then added with stirring, in an amount to yield a concentration of 9 g/L, to give final treating bath No. A.

Final treating baths B through K were prepared by the same general procedure as for treating bath No. A, but with the compositions reported in Table 1.

(2) Treatment Method

Using the process sequence outlined below, the treatment solutions thus formulated were applied to the surfaces of electrogalvanized steel sheets and zinc-nickel alloy electroplated steel sheets and dried to obtain products with the characteristics reported in Table 2.

steel sheet to be treated(*1) ⟶ alkali degreasing(*2) ⟶ water rinse ⟶ roll squeezing ⟶ drying (air current drying). ⟶ treating with a composition according to this invention ⟶ roll squeezing ⟶ drying(*3) ⟶ evaluation testing.

Notes on the Process Sequence (*1) The steel sheets subjected to this treatment consisted of duplex electrogalvanized steel sheet (quantity of zinc plating = 20 g/m², 20 g/m²) and duplex zinc-nickel alloy electroplated steel sheet (plating quantity = 20 g/m², 20 g/m², containing 11 weight % nickel). The size was 200 × 300 mm, and oiled material with a sheet thickness of 0.8 mm was used.

(*2) Alkali degreasing was carried out using a 2 % aqueous solution of a weakly alkaline degreaser (Par-Clean ® 342 from Nihon Parkerizing Company, Limited, Tokyo) by spraying at 60 degrees Centigrade for 30 seconds.

(*3) Drying was carried out at a sheet temperature of 100 degrees Centigrade for a drying time of 7 seconds.

TABLE 2

|  | | | | | properties | | | | | | |
| --- | --- | --- | --- | --- | --- | --- | --- | --- | --- | --- | --- |
|  | type of zinc-plated steel sheet* | chromate bath | chromate adherence mg/m² | alkali resistance % | corrosion resistance | | corrosion resistance of the painted sheet (mm) | | paint adherence | | welding resistance |
|  | | | | | before alkali rinse | after alkali rinse | before alkali rinse | after alkali rinse | cross-cut test | Erichsen extrusion test | |
| present invention | | | | | | | | | | | |
| No. 1 | EG | No. A | 80 | 2 | ++ | ++ | 1.0 | 1.0 | ++ | ++ | — |
| No. 2 | " | No. B | 50 | 0 | + | + | 1.0 | 1.0 | ++ | ++ | — |
| No. 3 | " | No. C | 15 | 0 | + | + | 1.5 | 1.5 | + | + | — |
| No. 4 | " | No. D | 100 | 3 | ++ | ++ | 1.0 | 0.5 | ++ | ++ | — |
| No. 5 | " | No. E | 50 | 4 | ++ | + | 1.0 | 1.5 | ++ | ++ | — |
| No. 6 | " | No. F | 180 | 2 | ++ | ++ | 0.5 | 0.5 | ++ | + | — |
| No. 7 | Zn—Ni | No. A | 80 | 3 | ++ | + | 0.5 | 0.5 | ++ | + | ≧ 1000 spots |
| No. 8 | " | No. B | 50 | 2 | + | + | 0.5 | 0.5 | ++ | ++ | " |
| No. 9 | " | No. C | 15 | 0 | + | + | 1.0 | 1.5 | + | + | " |
| No. 10 | " | No. D | 100 | 1 | ++ | ++ | 0.5 | 0.5 | ++ | + | " |
| No. 11 | " | No. E | 50 | 0 | + | + | 0.5 | 1.0 | ++ | ++ | " |
| No. 12 | " | No. F | 180 | 5 | ++ | ++ | 0.5 | 0.5 | ++ | + | " |
| comparison examples | | | | | | | | | | | |
| No. 1 | EG | No. C | 8 | 0 | x | x | 3.5 | 4.0 | Δ | x | — |
| No. 2 | " | No. G | 70 | 30 | + | x | 2.0 | 2.5 | + | + | — |
| No. 3 | " | No. H | 50 | 40 | Δ | x | 2.5 | 3.0 | Δ | Δ | — |

TABLE 2-continued

| | type of zinc-plated steel sheet* | chromate bath | chromate adherence mg/m² | alkali resistance % | corrosion resistance before alkali rinse | corrosion resistance after alkali rinse | corrosion resistance of the painted sheet (mm) before alkali rinse | corrosion resistance of the painted sheet (mm) after alkali rinse | paint adherence cross-cut test | paint adherence Erichsen extrusion test | welding resistance |
|---|---|---|---|---|---|---|---|---|---|---|---|
| No. 4 | " | No. I | 70 | 50 | Δ | x | 1.5 | 2.5 | Δ | x | — |
| No. 5 | " | No. J | 80 | 70 | + | x | 2.0 | 3.0 | Δ | Δ | — |
| No. 6 | Zn—Ni | No. C | 8 | 1 | x | x | 2.0 | 3.0 | x | x | ≧1000 spots |
| No. 7 | " | No. G | 70 | 40 | Δ | x | 1.0 | 2.0 | + | Δ | " |
| No. 8 | " | No. J | 80 | 80 | + | x | 1.5 | 2.5 | Δ | x | " |
| No. 9 | " | No. K | 50 | 25 | ++ | + | 1.0 | 2.0 | Δ | Δ | ≦800 spots |

Notes:
*EG: electrogalvanized steel sheet
Zn—Ni: zinc-nickel alloy electroplated steel sheet (3) Preparation of Painted Sheets The treated zinc coated steel, either as such or after the alkali rinse described below in item (4)(a), was painted with a bakeable melamine alkyd paint (Delicon ™ 700 White from Dainippon Paint Company, Limited) and then baked for 20 minutes at 140 degrees Centigrade to give a painted sheet carrying a 25 micrometer thick coating.

(4) Property Evaluation Testing (a) Alkali resistance test

The treated sheet was alkali rinsed using the conditions specified below, and the quantity of adhering chromium in mg/m² was measured by X-ray fluorescence both before and after this rinse. The "alkali resistance" as reported in Table 2 is defined as the percentage of the chromium originally present that is removed by this rinsing. Thus, the alkali resistance increases as the percent value declines, and a zero value indicates absolutely no loss from alkali in this test, or complete resistance. The alkali rinse conditions were as follows: 2 minute spray at 60 degrees Centigrade using a 2% aqueous solution of a sodium silicate-based alkaline degreaser (Par-Clean® N364S from Nihon Parkerizing Company, Limited).

(b) Corrosion Resistance

1. Electrogalvanized steel sheet

Each test specimen (70×150 mm) was evaluated before and after the alkali rinse using the salt-spray test specified in Japanese Industrial Standard ("JIS") Z-2371 for 150 hours. The corrosion resistance was evaluated on the basis of the development of white rust by surveying the entire area of the test specimen and reported using the following symbols:

++: area of white rust development=0%
+: area of white rust development<10%
Δ: area of white rust development≧10%, but<30%
x: area of white rust development≧30%

2. Zinc-nickel alloy electroplated steel sheet

The test specimen was subjected to a composite corrosion test (50 cycles) both before and after alkali rinsing. Each cycle consisted of salt spray for 4 hours, drying at 60 degrees Centigrade for 2 hours, and wetting at 50 degrees Centigrade and a relative humidity of ≧95% for 2 hours. The corrosion resistance was evaluated on the basis of the development of red rust by surveying the entire area of the test specimen and reported according to the symbols below.

++: area of red rust development=0%
+: area of red rust development<10%
Δ: area of red rust development≧10%, but<30%
x: area of red rust development≧30%

(c) Corrosion Resistance of the Painted Sheet

Using a cutter, a cut which reached to the base metal was introduced in the paint film. This was followed by salt-spray testing for 200 hours for the electrogalvanized steel sheet and 300 hours for the zinc-nickel alloy electroplated steel sheet. Conventional transparent adhesive tape was then applied over the area of the cut and then peeled off. The value reported in the Table is the maximum width in mm of peeling of paint from one side of the cut.

(d) Paint Adherence

1. Crosscut test

Using a cutter, a checkerboard of 1 mm squares was scribed to the base metal on the painted test specimen (with no alkali rinse). Adhesive tape was applied to this and then rapidly peeled off, and the degree of peeling of the paint film was subsequently inspected. Results are reported with the same symbols as for the corrosion tests noted above, with the % of area of paint removed in peeling substituted for the area covered with red or white rust.

2. Erichsen Extrusion Test

Using an Erichsen extruder, the painted test specimen (with no alkali rinse) was extruded 6 mm. Conventional transparent adhesive tape was then applied and rapidly peeled off, and the degree of paint film peeling was inspected and reported with the same symbols as for the crosscut test.

(e) Ease of Welding

When spot welding is conducted continuously on zinc-nickel alloy electroplated steel sheet under the conditions given below, the welding tip gradually deteriorates and the weld quality becomes poor. Accordingly, the ease of welding can be judged from the number of spot welds of adequate quality that can be made with a single set of welding electrodes. Thus, several separate 30×100 mm test specimens were welded with 100 spots each with a single set of welding electrodes, and the number of spots for which the test specimens maintained a tensile shear strength of 400 kg was recorded. Welding conditions included an applied force of 200 kilograms, a current of 8.5 kiloamperes for 10 cycles of the current for each welding spot, and radius type electrodes of chromium-copper.

(f) Test of the Uniformity of Coating of the Treatment Bath

Water-soluble organic solvent was added to bath No. G as reported in Table 1, and the uniformity of application of the chromate film by roll coating application was evaluated. This evaluation is reported in Table 3 along with the surface tension of the chromate bath. The coating uniformity of the chromate film was evaluated on the basis of the following three-level scale: + = uniform; Δ = slight cissing; x = substantial cissing.

TABLE 3

| | | chromate bath | | | surface tension (dyn/cm) | coating uniformity of the chromate bath | |
| --- | --- | --- | --- | --- | --- | --- | --- |
| | | $Cr^{+6}$ (g/L) | $Cr^{+3}$ (g/L) | water-soluble organic solvent (g/L) | | line speed 70 m/min | line speed 150 m/min |
| within the scope of the invention | No. 1 | 20 | 15 | t-butanol 5 | 60 | + | + |
| | No. 2 | 20 | 15 | t-butanol 10 | 50 | + | + |
| | No. 3 | 20 | 15 | t-butanol 20 | 45 | + | + |
| | No. 4 | 20 | 15 | t-amyl alcohol 15 | 50 | + | + |
| | No. 5 | 20 | 15 | acetonitrile 45 | 61 | + | + |
| outside the scope of the invention | No. 1 | 20 | 15 | — | 70 | Δ | x |
| | No. 2 | 20 | 15 | t-butanol 2 | 67 | + | Δ |

BENEFITS OF THE INVENTION

When the chromate film contains silane coupling agent in the amounts taught according to this invention, an excellent paint adherence is observed, as in Examples 1 to 12, while a poor paint adherence is observed in Comparison Examples 3, 5, and 8, which lack silane coupling agent, and in Comparison Examples 1, 4, and 6, in which the quantity of one or more constituents of the treating solution falls outside the scope of the claims.

As explained above, practice of the present invention forms a surface film which is very uniformly distributed over the surface of zinc objects, especially zinc-plated steel sheet. The treated sheet is well suited to welding, resistant to alkali treatment and corrosion, and very well adapted for painting, because paint adheres very well and the painted surface is corrosion resistant.

What is claimed is:

1. A process for treating an object with a zinciferous surface, said process comprising steps of:
   (A) contacting the surface of the object to be treated with a liquid solution composition that consists essentially of water and the following components:
   (1) from about 3.0 to about 50 g/L of hexavalent chromium;
   (2) from about 2.0 to about 40 g/L of trivalent chromium
   (3) from about 1.0 to about 100 g/L of phosphate ion;
   (4) from about 3 to about 50 g/L of organic material selected from acetonitrile, tertiary alcohols with from about 4 to about 8 carbon atoms per molecule, and mixtures of any two or more of these; and
   (5) an amount of silane coupling agent such as to yield a ratio of about 0.05 to about 0.30 between the total molar concentration of silane coupling agent and the gram atomic concentration of hexavalent chromium concentration in the composition; and, optionally,
   (6) from about 0.2 to about 10 g/L of $Zn^{+2}$ ions; and
   (7) a component selected from fluoride ions, complex fluoride ions, and mixtures of any two or more of these in an amount to give a concentration in the composition of from about 0.2 to about 8 g/L of stoichiometric equivalent of fluoride, the $Cr^{3+}:Cr^{6+}$ weight ratio in the solution being about 0.25 to about 1.5 and the weight ratio between phosphate ion and total chromium being about 0.1 to about 1.2; and
   (B) drying the surface contacted in step (A) while there remains distributed over said surface nonvolatile constituents derived from the liquid solution composition with which the surface is contacted in step (A), so as to form on the surface a chromium containing film with a chromium content of about 10 to about 200 milligrams per square meter.

2. A process according to claim 1, wherein component (4) is selected from the group consisting of 2-methyl-2-propanol, 2-methyl-2-butanol, and mixtures thereof.

3. A process according to claim 2, wherein component (5) is selected from materials conforming to the general formula $Y_yR_rSiX_x$, wherein R represents an alkyl group; X represents a group selected from methoxy and ethoxy groups; Y represents a group selected from a vinyl group, a mercapto group, a glycidoxyalkyl group, or a methacryloxyalkyl group; and each of r, x, and y is an integer independently selectable from 1–3, except that r may also be zero and that the sum r+x+y=4.

4. A process according to claim 1, wherein component (5) is selected from materials conforming to the general formula $Y_yR_rSiX_x$, wherein R represents an alkyl group; X represents a group selected from methoxy and ethoxy groups; Y represents a group selected from a vinyl group, a mercapto group, a glycidoxyalkyl group, or a methacryloxyalkyl group; and each of r, x, and y is an integer independently selectable from 1–3, except that r may also be zero and that the sum r+x+y =4.

5. A process according to claim 4, wherein component (6) is present and the counterions are selected from the group consisting of hydroxide, carbonate, phosphate, and mixtures thereof.

6. A process according to claim 3, wherein component (6) is present and the counterions are selected from the group consisting of hydroxide, carbonate, phosphate, and mixtures thereof.

7. A process according to claim 2, wherein component (6) is present and the counterions are selected from the group consisting of hydroxide, carbonate, phosphate, and mixtures thereof.

8. A process according to claim 1, wherein component (6) is present and the counterions are selected from the group consisting of hydroxide, carbonate, phosphate, and mixtures thereof.

9. A process according to claim 8, wherein component (7) is present and is selected from the group consisting of fluozirconic acid, fluotitanic acid, fluosilicic acid, fluoboric acid, and mixtures thereof.

10. A process according to claim 7, wherein component (7) is present and is selected from the group consisting of fluozirconic acid, fluotitanic acid, fluosilicic acid, fluoboric acid, and mixtures thereof.

11. A process according to claim 6, wherein component (7) is present and is selected from the group consisting of fluozirconic acid, fluotitanic acid, fluosilicic acid, fluoboric acid, and mixtures thereof.

12. A process according to claim 5, wherein component (7) is present and is selected from the group consisting of fluozirconic acid, fluotitanic acid, fluosilicic acid, fluoboric acid, and mixtures thereof.

13. A process according to claim 4, wherein component (7) is present and is selected from the group consisting of fluozirconic acid, fluotitanic acid, fluosilicic acid, fluoboric acid, and mixtures thereof.

14. A process according to claim 3, wherein component (7) is present and is selected from the group consisting of fluozirconic acid, fluotitanic acid, fluosilicic acid, fluoboric acid, and mixtures thereof.

15. A process according to claim 2, wherein component (7) is present and is selected from the group consisting of fluozirconic acid, fluotitanic acid, fluosilicic acid, fluoboric acid, and mixtures thereof.

16. A process according to claim 1, wherein component (7) is present and is selected from the group consisting of fluozirconic acid, fluotitanic acid, fluosilicic acid, fluoboric acid, and mixtures thereof.

17. A process according to claim 16, wherein the temperature of the treated object during step (B) is between about 60 and about 150 degrees Centigrade and the time of drying is in the range from about 5 to about 10 seconds.

18. A process according to claim 12, wherein the temperature of the treated object during step (B) is between about 60 and about 150 degrees Centigrade and the time of drying is in the range from about 5 to about 10 seconds.

19. A process according to claim 2, wherein the temperature of the treated object during step (B) is between about 60 and about 150 degrees Centigrade and the time of drying is in the range from about 5 to about 10 seconds.

20. A process according to claim 1, wherein the temperature of the treated object during step (B) is between about 60 and about 150 degrees Centigrade and the time of drying is in the range from about 5 to about 10 seconds.

* * * * *